United States Patent [19]
Church

[11] Patent Number: 5,829,466
[45] Date of Patent: Nov. 3, 1998

[54] FLUID TREATMENT SYSTEM

[75] Inventor: Garry Church, Beverley, England

[73] Assignee: Lasertrim Ltd., Hull, United Kingdom

[21] Appl. No.: 817,105

[22] PCT Filed: Oct. 13, 1995

[86] PCT No.: PCT/GB95/02437

§ 371 Date: Apr. 7, 1997

§ 102(e) Date: Apr. 7, 1997

[87] PCT Pub. No.: WO96/11883

PCT Pub. Date: Apr. 25, 1996

[30]     Foreign Application Priority Data

Oct. 13, 1994 [GB] United Kingdom .................. 9420627

[51] Int. Cl.$^6$ ..................................................... E03B 1/00
[52] U.S. Cl. .................................. 137/4; 137/89; 137/92; 137/93; 137/5
[58] Field of Search ................................. 137/88, 92, 89, 137/98, 101.19, 3, 4, 5, 93

[56] References Cited

U.S. PATENT DOCUMENTS

| 4,031,912 | 6/1977 | Lu ............................................. 137/89 |
| 4,855,061 | 8/1989 | Martin . |

FOREIGN PATENT DOCUMENTS

| 0 415 726 A1 | 3/1991 | European Pat. Off. . |
| 4112391A1 | 10/1992 | Germany . |
| 0068458 | 5/1983 | United Kingdom . |
| 2235782 | 3/1991 | United Kingdom . |

Primary Examiner—Denise L. Ferensic
Assistant Examiner—Ramyar Farid
Attorney, Agent, or Firm—Hopgood, Calimafde, Kalil & Judlowe, LLP

[57]                  ABSTRACT

A system and method for treating a fluid flowing along a main fluid supply path in which a streaming current detector receives a sample flow of a main fluid supply following main dosing with a chemical under control of a streaming current detector output. A secondary chemical dosing is applied to the sample under the control of the streaming current detector output in a feedback loop.

18 Claims, 5 Drawing Sheets

FLUID TREATMENT SYSTEM

This invention relates to a fluid treatment system which includes a device, such as a streaming current detector (SCD), for measuring the charge in a fluid sample. The invention may be used in the paper-making field, where a suspension of finely divided particles are made to coagulate by the addition of a flocculating agent, the dosing of the flocculating agent being controlled in accordance with measurements taken from the charge-measuring device.

A streaming current detector (SCD) is an instrument which is used to detect the charge condition in a fluid, such as water. The data obtained by this charge detection can be used for the control and monitoring of various water based processes.

A number of instruments using the so-called streaming current principle have been developed over the years, one example being disclosed in our UK Patent No. 235 782 and illustrated in FIG. 1 of the accompanying drawings. The cell 10 illustrated receives at its inlet 32 a sample fluid tapped via a sample supply line 20 from a main fluid supply 15. The sample fluid enters a sample chamber 33 in the form of a through passageway and passes over a sample cell 38 and out to drain via fluid outlet 34. The reciprocating movement of a piston 42 by a motor (not shown) within the bore of an insulating body 39 repeatedly draws a small sample of fluid from the flow of fluid through the chamber 33 down into the measuring cell 38 and the resultant charge measurement is made across annular electrodes 51 and 50 set into the cylindrical wall of the bore in the insulating body 39.

The above general principal of streaming current detection using a reciprocating piston and spaced electrodes in the piston receiving bore of an insulating body is used by a number of manufacturers of streaming current detectors.

In a fluid treatment system illustrated in FIG. 2 in which a chemical A which is being used to treat the main fluid supply for coagulation or flocculation of the liquid is added to the main fluid supply 15 line 20, the sample which is applied to the above streaming current cell will contain this chemical A. This chemical provided the predominant background charge and the signal output from the SCD cell 10, which signal can be employed as a feedback in the dosing control equipment, is therefore attributable mainly to this background charge. A typical block diagram of a simple fluid treatment system is provided in FIG. 2. Where the chemical has been added to the main fluid, the quality of the sample supply is then determined by the streaming current detector which will measure the resultant charge of both chemical addition and sample quality. Assuming a given rate of dosing of the chemical A, any variation of the signal output from a predetermined setpoint associated with that dosing rate can only be due to variation in the sample quality. The dosing rate can then be adjusted accordingly.

Automation of this system is effected in a manner illustrated in FIG. 3. In this FIG. 3 system, the signal 11 from the SCD 10 is connected to a process controller 54 which will monitor the changing sample quality and adjust the rate of chemical addition to the main fluid, to restore the SCD signal to the predetermined setpoint.

This feedback control technique employed in the system shown in the configuration in FIG. 3 is used in the majority of coagulation control systems which are in use at the present time.

While this feedback technique for fluid monitoring and treatment may be satisfactory when used in a relatively simple system, for example in a water supply/purification plant, where there are no other significant influences upon the charge level in the sample supply, the system's effectiveness is much reduced in more complex applications, such as in the paper-making and sewage treatment industries. Here, numerous other influences and chemicals have an effect on the fluid supply under test, eg. on the fluid paper stock, and these will so affect the charge condition of the sample supply as to the overwhelm the influence of the particular chemical A (for flocculation/coagulation) on the overall charge condition. As the SCD cell is incapable of distinguishing between these different causes of charge condition variation, its output could produce, through the automatic feedback loop, a variation in the chemical A dosing which is unrelated to the actual dosing requirement in the main fluid supply.

The present invention is directed to alleviating this problem, and to that end provides a fluid treatment system in which a steaming current detector (SCD) is arranged to receive a sample of a fluid supply following main dosing with a chemical and control of the main dosing is effected in accordance with the SCD output, wherein a secondary chemical dosing is applied to the sample under the control of the SCD output in a feedback control loop and wherein the signal from the SCD is supplied to a sample dosing controller in said feedback and is used to control the main dosing.

As the secondary chemical dosing is applied to the sample, the effect of the secondary chemical dosing is seen directly by the SCD. Thus it can be assured that restoration of the SCD's signal to the setpoint has resulted from a correct level of the secondary chemical dosing of the sample.

In the described embodiments the output of the sample dosing controller (the SCD controlled output) is used to control both the secondary chemical dosing and the main dosing.

In a system where the main dosing is controlled automatically using the SCD controlled output, the dosing rate for the main supply chemical may be adjusted in proportion to the variation in the SCD controlled output signal; this latter variation represents the required variation in the secondary chemical dosing to re-establish the SCD setpoint.

Preferably, the fluid supply sample is in the form of a fluid stream which flows continuously through the SCD cell.

In some cases the main and secondary chemical dosing are preformed using the same chemical.

Preferred embodiments of the invention will now be described by way of example with reference to the accompanying drawings, in which.

Figure 1:
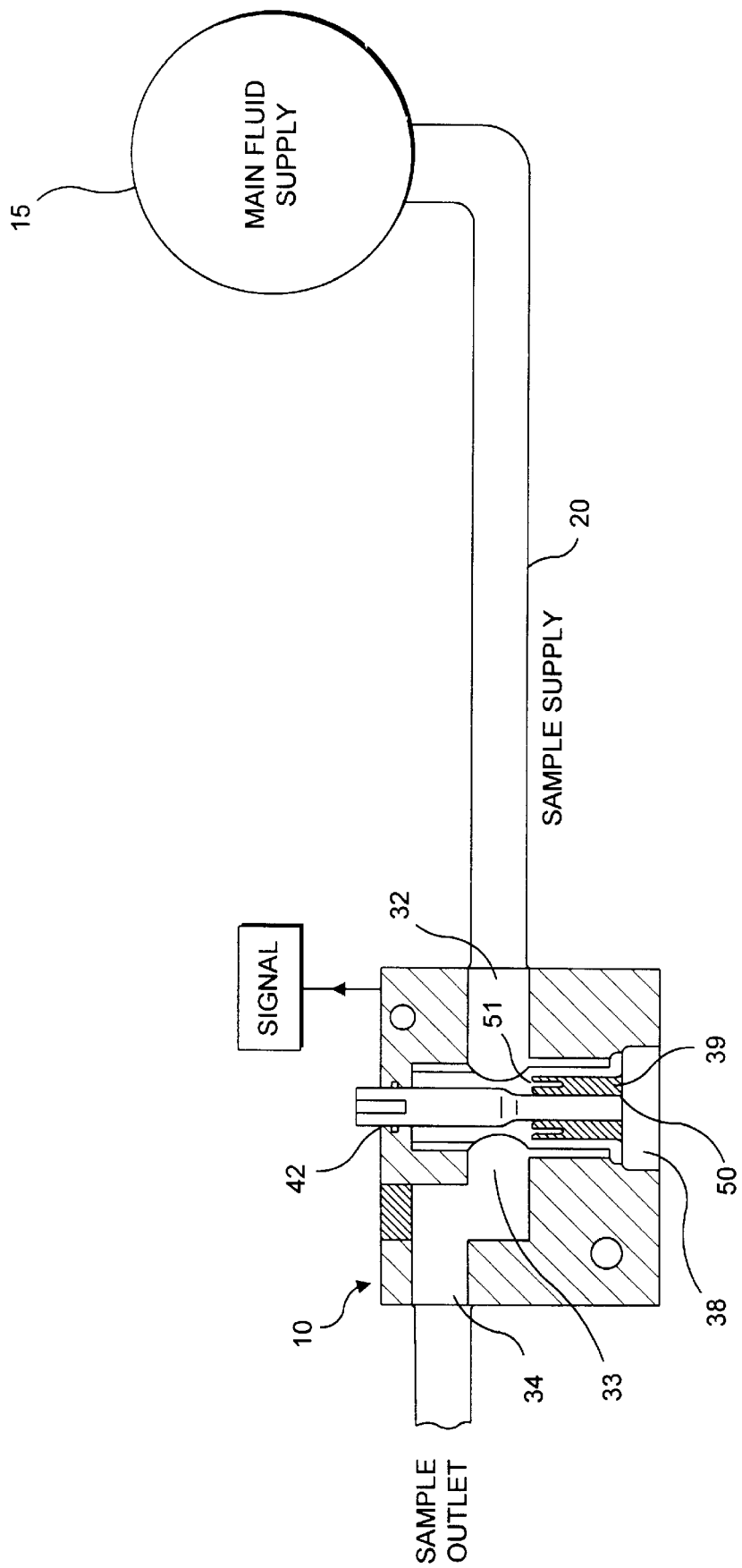
FIG. 1 illustrates the use of a SCD cell in accordance with our UK patent 2 235 792 for monitoring a fluid sample supply.
Figure 2:
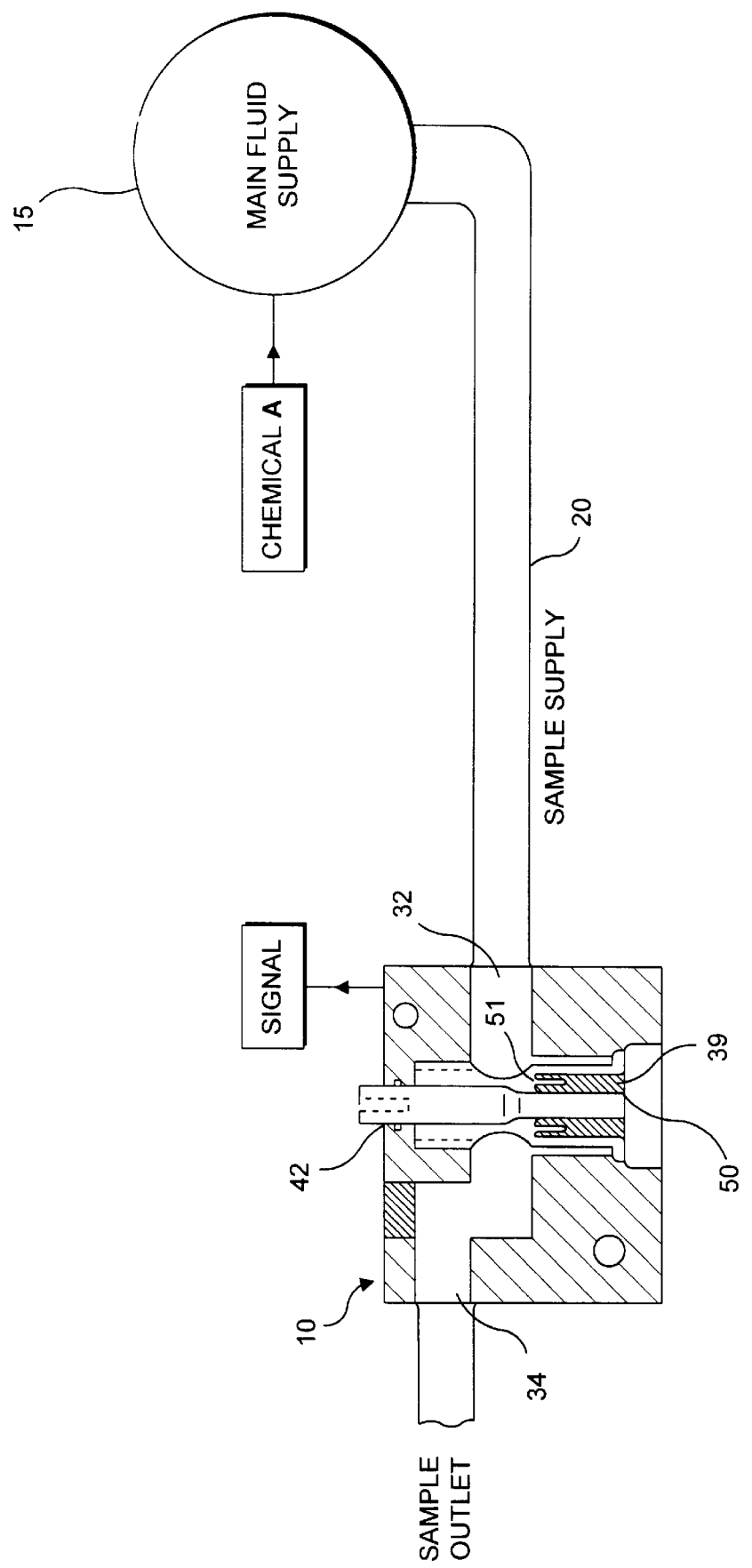
FIG. 2 illustrates such SCD cell used in a known manner in a simple fluid treatment system.
Figure 3:
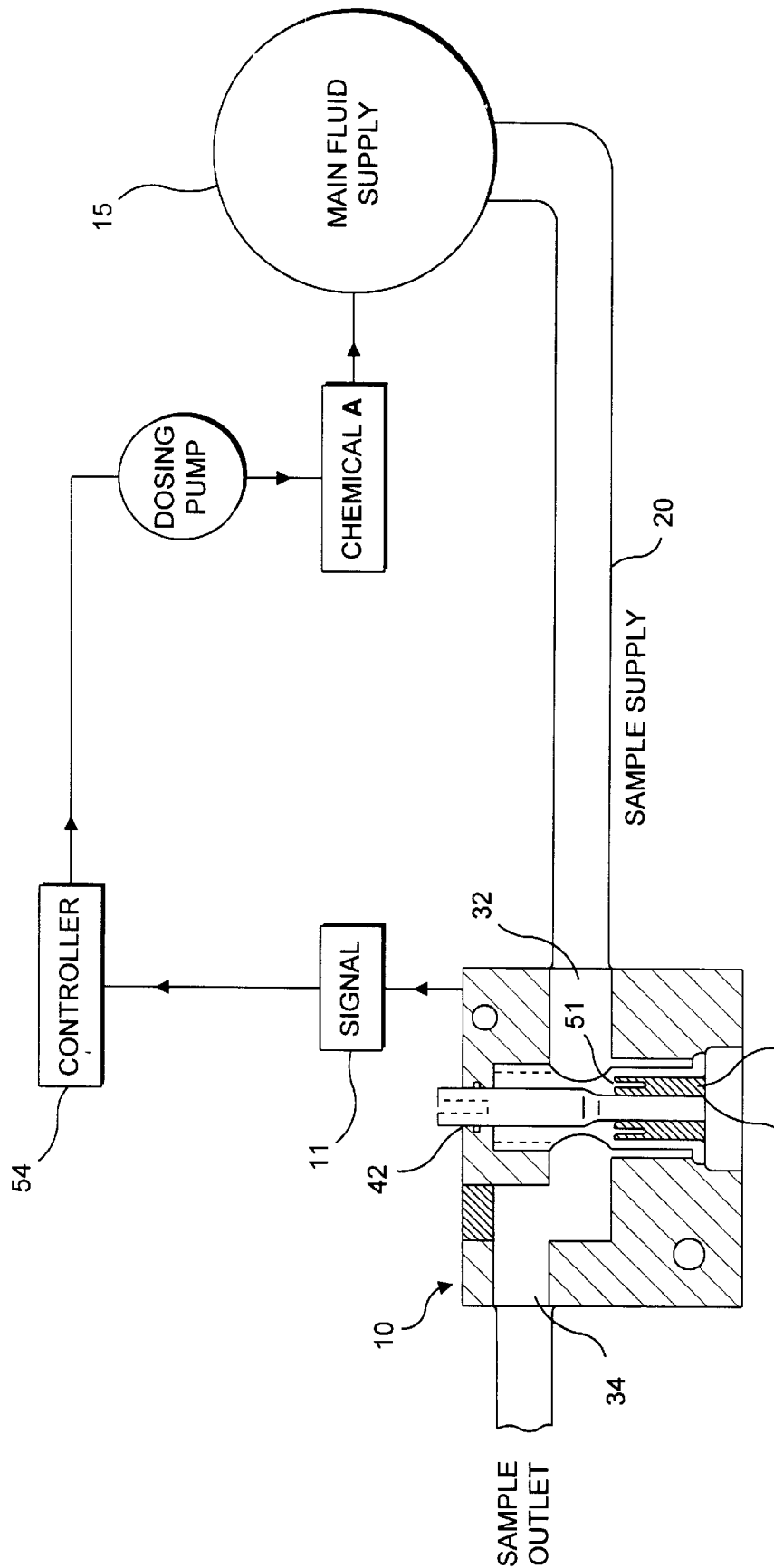
FIG. 3 illustrates the SCD cell used in a known automatic fluid treatment system.
Figure 4:
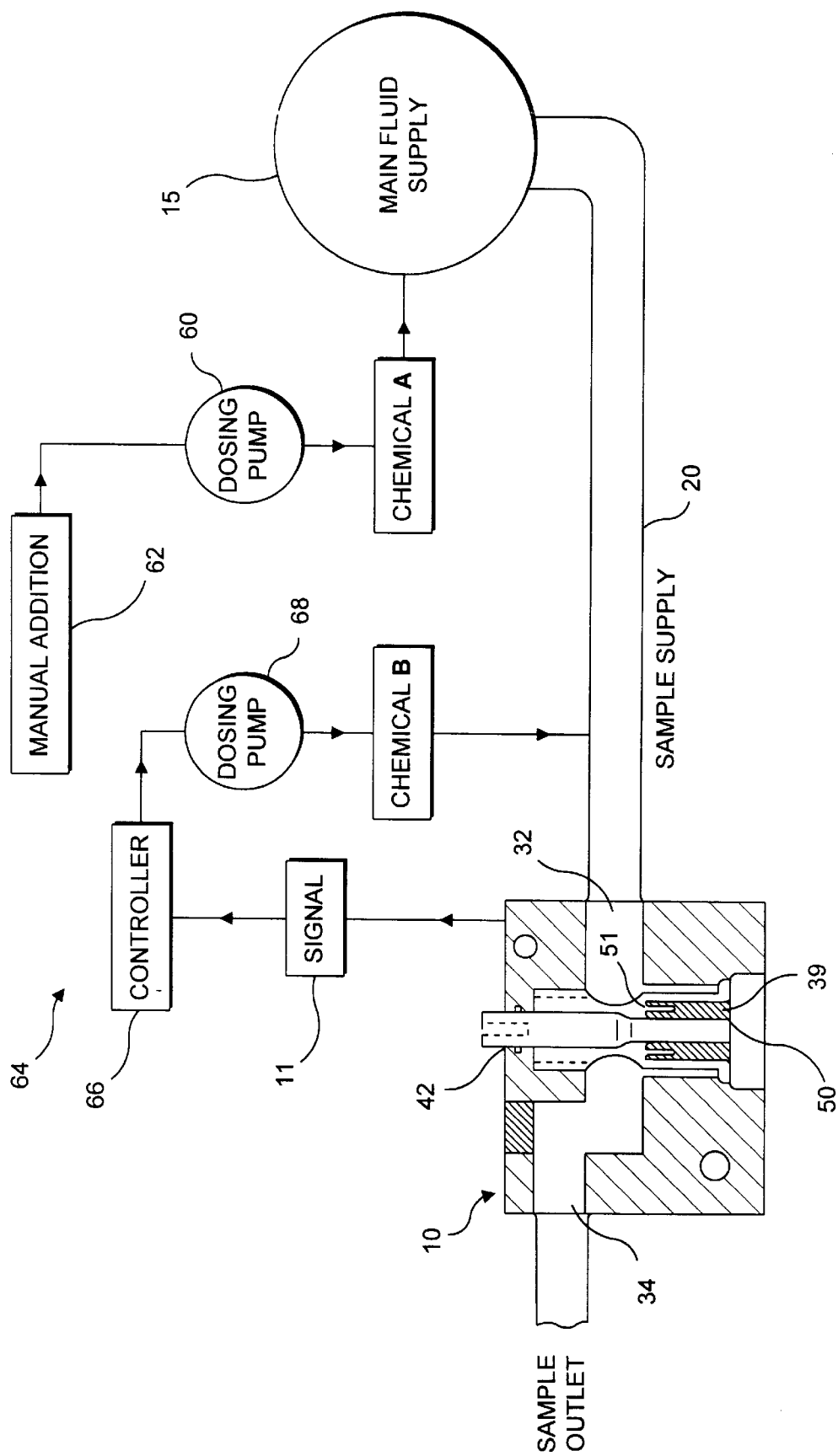
FIG. 4 illustrates the cell used in a fluid treatment system in accordance with the present invention, with manual main dosing control.

With reference first to FIG. 4, in which the same reference numerals as used in FIGS. 1 to 3 are employed to refer to corresponding system components, a fluid treatment system 1 is applied to a main fluid supply 15, for example a liquid paper stock supply to a paper-making machine or an effluent supply in a sewage treatment system. A sample supply line 20 leads from the main supply 15 to a SCD cell 10 as before; further explanation of the construction and operation of the cell 10, described earlier herein, is considered unnecessary.

Again a main dosing chemical A for flocculating, or coagulating, a fluid containing suspended particles is introduced into the main supply 15 upstream of the tap-off point of the sample supply line 20. In this particular embodiment a dosing pump 60 for feeding the main dosing chemical A is manually controlled by way of a manual control unit 62.

An additional, a secondary chemical dosing is applied directly to the sample supply line 20 upstream of the SCD cell 10. The secondary chemical, referred to as chemical B which may be the same chemical as chemical A, is also a flocculating agent. The output signal 11 of the SCD cell 10 is connected in a feedback control loop 64 to its own controller 66 so as to control the dosing of the chemical B into the sample fluid supply by a secondary dosing pump 68. The controller 66 is arranged to so control the secondary chemical dosing as to maintain the signal 11 at an internal predetermined setpoint corresponding with a desired charge condition, which may be a zero charge condition known in the art as isoelectric zero. Thus, the secondary chemical dosing rate is such as to effect neutralisation of the charged sample fluid, and the SCD controlled output (output from the controller 66) is a measure of the total charge condition or cationic demand of the sample fluid supply.

Again, for a given dosing rate of chemical B, any variation in signal 11 from the setpoint represents a change in the charge condition of the sample fluid and therefore of the fluid in the main fluid supply. For a given dosing rate of chemical A, this change in the charge condition of the main supply fluid will be due to other influences upon the charge condition (the main flow cationic demand), such as variation in the dosing levels of other additives.

Since the control loop 64 acts around the SCD itself in the sample supply, the effect of the chemical B dosing is seen directly by the SCD, and it cam be assured that restoration of the SCD's signal to the setpoint has resulted from a correct level of the chemical B dosing required to satisfy the cationic demand in the sample supply.

Knowing the flow rates in the main and sample fluids and the dosing rate of chemical B (i.e. the cationic demand in the sample fluid) it is a simple matter then to calculate the cationic demand of the main fluid using the flow rate ratio, and then to apply this parameter to the manual control of the pump 60 by way of the manual control unit 62.

As the effectiveness of chemical A for flocculation/coagulation of the main fluid supply is heavily dependent upon the main fluid cationic demand, the main flow cationic demand is the primary variable control parameter for the main chemical dosing. A predetermined control function relates this main flow cationic demand to main chemical dosing rate.

Figure 5:
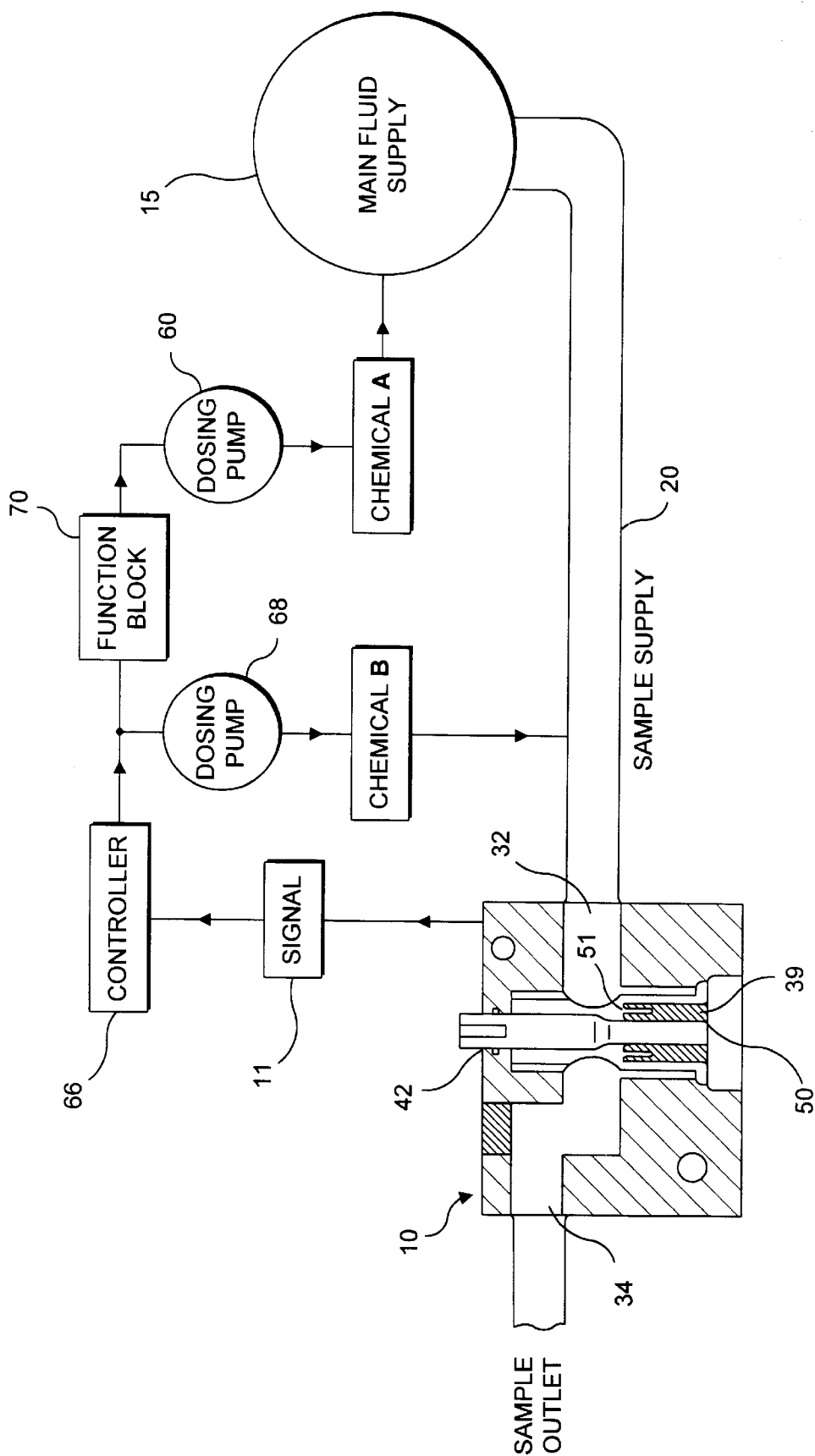
FIG. 5 illustrates the cell used in another fluid treatment system in accordance with the present invention, with automatic main dosing control.

Automation of the system of the first embodiment in FIG. 4 can be achieved as shown in FIG. 5 by adding a function controller 70 which takes the output from the SCD feedback loop controller 66 as applied to the dosing pump and automatically applies the aforesaid ratio of main flow rate-:sample flow rate so as to scale up the dose rate for determination of main flow cationic demand and appropriate control of the main dosing pump 60.

The above described embodiments can achieve proper control of the flocculant/coagulant additive in complex fluid treatment systems where there are other influences on the fluid charge condition.

I claim:

1. A system for treating a fluid flowing along a main fluid supply path comprising:
   first dosing means for applying a primary chemical dosing to the fluid at a dosing point in said main fluid supply path;
   means for taking a sample flow of the fluid from a point in said main fluid supply path downstream of said dosing point;
   a streaming current detector arranged to receive said sample flow; and
   means permitting said primary chemical dosing to be controlled in accordance with the streaming current detector output; characterised by a second dosing means for applying a secondary chemical dosing to the sample flow, and a feedback control loop including said second dosing means and a sample dosing controller arranged to receive the streaming current detector output and to control the second dose means in accordance with the streaming current detector output.

2. A system according to claim 1, wherein the sample dosing controller is arranged to control both the second dosing means in said feedback loop and the first dosing means, with a means being provided for automatically controlling said first dosing means in accordance with the output of said sample dosing controller.

3. A system according to claim 1, wherein said streaming current detector is adapted to receive and convey a flow of fluid from an inlet thereof to an outlet thereof via a through passageway formed therein.

4. A system according to claim 2, wherein said streaming current detector is adapted to receive and convey a flow of fluid from an inlet thereof to an outlet thereof via a through passageway formed therein.

5. A system according to claim 3, wherein said streaming current detector is arranged to receive a continuous flow of said sample taken from the main fluid supply path.

6. A system according to claim 4, wherein said streaming current detector is arranged to receive a continuous flow of said sample taken from the main fluid supply path.

7. A system according to claim 1, wherein said first and second dosing means comprise respective dosing pumps for introducing said main chemical dosing into the main fluid supply path, and for introducing said secondary chemical dosing into the sample flow, respectively.

8. A system according to claim 2, wherein said first and second dosing means comprise respective dosing pumps for introducing said main chemical dosing into the main fluid supply path, and for introducing said secondary chemical dosing into the sample flow, respectively.

9. A system according to claim 3, wherein said streaming current detector includes a piston-receiving body arranged to one side of said through passageway, a piston reciprocal within a bore of said body for repetitively drawing fluid samples into said bore from the fluid flowing in said passageway, and electrodes spaced apart along said bore and exposed to said fluid samples for generating an output signal representing the charge condition of said sample fluid.

10. A system according to claim 4, wherein said streaming current detector includes a piston-receiving body arranged to one side of said through passageway, a piston reciprocal within a bore of said body for repetitively drawing fluid samples into said bore from the fluid flowing in said passageway, and electrodes spaced apart along said bore and exposed to said fluid samples for generating an output signal representing the charge condition of said sample fluid.

11. A system according to claim 5, wherein said streaming current detector includes a piston-receiving body arranged to one side of said through passageway, a piston reciprocal within a bore of said body for repetitively drawing fluid samples into said bore from the fluid flowing in said passageway, and electrodes spaced apart along said bore and exposed to said fluid samples for generating an output signal representing the charge condition of said sample fluid.

12. A system according to claim 6, wherein said streaming current detector includes a piston-receiving body arranged to one side of said through passageway, a piston reciprocal within a bore of said body for repetitively drawing fluid samples into said bore from the fluid flowing in said passageway, and electrodes spaced apart along said bore and exposed to said fluid samples for generating an output signal representing the charge condition of said sample fluid.

13. A fluid treatment method in which a streaming current detector receives a sample flow of a main fluid supply following main dosing with a chemical and control of the main dosing is effected in accordance with the streaming current detector output, wherein a secondary chemical dosing is applied to the sample under the control of the streaming current detector output in a feedback control loop and wherein the signal from the streaming current detector is both supplied to a sample dosing controller in said feedback loop and is used to control the main dosing.

14. A fluid treatment method according to claim 13, wherein said main dosing and said secondary dosing use the same chemical.

15. A fluid treatment method according to claim 13, wherein the sample dosing controller is used to control both the secondary chemical dosing by way of said feedback loop, and the main dosing by automatic control means which receives the output of said sample dosing controller.

16. A fluid treatment method according to claim 14, wherein the sample dosing controller is used to control both the secondary chemical dosing by way of said feedback loop, and the main dosing by automatic control means which receives the output of said sample dosing controller.

17. A fluid treatment system according to claim 15, wherein said automatic control means automatically determines the cationic demand of the main fluid supply from the cationic demand of the sample flow as represented by said output of the sample dosing controller, in accordance with the ratio between the respective fluid flow rates of the main and sample flows.

18. A fluid treatment system according to claim 16, wherein said automatic control means automatically determines the cationic demand of the main fluid supply from the cationic demand of the sample flow as represented by said output of the sample dosing controller, in accordance with the ratio between the respective fluid flow rates of the main and sample flows.

* * * * *